United States Patent [19]

Gerhardt et al.

[11] Patent Number: 4,474,807
[45] Date of Patent: Oct. 2, 1984

[54] 2-(3-IODO-2-PROPYNYLOXY)-ETHYL CARBAMATES, THE PREPARATION THEREOF, AND THEIR USE AS ANTIMICROBIAL AGENTS

[75] Inventors: Werner Gerhardt, Hilden; Rudolf Lehmann, Neuss, both of Fed. Rep. of Germany

[73] Assignees: Henkel Kommandigesellschaft auf Aktien, Holthausen, Fed. Rep. of Germany; Montedison S.p.A., Milan, Italy

[21] Appl. No.: 427,881

[22] Filed: Sep. 29, 1982

[30] Foreign Application Priority Data

May 6, 1982 [DE] Fed. Rep. of Germany ....... 3216895

[51] Int. Cl.³ .................... A01N 47/12; A01N 47/20; C07C 125/065
[52] U.S. Cl. .................... 424/300; 560/12; 560/28; 560/30; 560/31; 560/32; 560/33; 560/115; 560/162; 560/164; 560/166
[58] Field of Search .............. 560/30, 31, 32, 33, 560/28, 10, 11, 12, 115, 162, 164, 166; 424/300

[56] References Cited

U.S. PATENT DOCUMENTS

| | | | |
|---|---|---|---|
| 2,197,479 | 4/1940 | Meigs | 560/162 |
| 2,806,838 | 9/1957 | Melamed | 560/162 |
| 3,012,067 | 12/1961 | Kaeding et al. | 424/300 |
| 3,226,426 | 12/1965 | Hopkins et al. | 560/166 |
| 3,439,021 | 4/1969 | Fancher | 560/164 |
| 3,639,455 | 2/1972 | Petersen et al. | 560/162 |
| 3,906,027 | 9/1975 | Meussdoerffer et al. | 560/12 |
| 3,923,870 | 12/1975 | Singer | 424/300 |
| 4,259,350 | 3/1981 | Morisawa et al. | 424/308 |

FOREIGN PATENT DOCUMENTS

| | | | |
|---|---|---|---|
| 14032 | 8/1980 | European Pat. Off. | 560/33 |
| 15044 | 9/1980 | European Pat. Off. | 560/33 |
| 884738 | 12/1961 | United Kingdom | 560/12 |

OTHER PUBLICATIONS

Chemical Abstracts, vol. 83, No. 13, 29; Sep. 1975, p. 492, No. 113679k.

Primary Examiner—Natalie Trousof
Assistant Examiner—Patricia M. Scott
Attorney, Agent, or Firm—Hammond, Littell, Weissenberger & Dippert

[57] ABSTRACT

This invention is directed to novel antimicrobial agents. More particularly, this invention is directed to 2-(3-iodo-2-propynyloxy)-ethyl carbamates of the formula

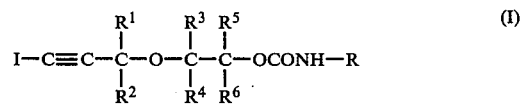

wherein R is hydrogen, linear or branched alkyl of from 1 to 12 carbon atoms, cycloalkyl of from 4 to 8 carbon atoms, aryl, substituted aryl, aralkyl, or arylsulfonyl;

$R^1$ and $R^2$, which may be the same or different, each are hydrogen, linear or branched alkyl or alkenyl of from 1 to 6 carbon atoms, or cycloalkyl of from 5 to 7 carbon atoms, or $R^1$ and $R^2$, taken together, represent $-(CH_2)_m-$, in which m is an integer of from 4 to 6; and $R^3$, $R^4$, $R^5$, and $R^6$, which may be the same or different, each represent hydrogen, alkyl of from 1 to 4 carbon atoms, or aryl, or $CCl_3$, or $R^3$ and $R^5$ or $R^4$ and $R^6$, taken together, represent $-(CH_2)_n-$, in which n is an integer of from 3 to 5, as well as a process for their preparation and their use as antimicrobial agents.

10 Claims, No Drawings

2-(3-IODO-2-PROPYNYLOXY)-ETHYL CARBAMATES, THE PREPARATION THEREOF, AND THEIR USE AS ANTIMICROBIAL AGENTS

FIELD OF THE INVENTION

This invention is directed to novel antimicrobial agents. More particularly, this invention is directed to 2-(3-iodo-2-propynyloxy)-ethyl carbamates, the preparation thereof, and their use as antimicrobial agents.

OBJECTS OF THE INVENTION

It is an object of the invention to provide novel antimicrobial agents.

It is also an object of the invention to provide 2-(3-iodo-2-propynyloxy)-ethyl carbamates of the formula

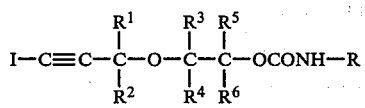

wherein

R is hydrogen, linear or branched alkyl of from 1 to 12 carbon atoms, cycloalkyl of from 4 to 8 carbon atoms, hydrocarbon aryl, halogen or lower alkyl substituted hydrocarbon aryl, hydrocarbon aralkyl, or hydrocarbon arylsulfonyl;

$R^1$ and $R^2$, which may be the same or different, each are hydrogen, linear or branched alkyl of from 1 to 6 carbon atoms, or alkenyl of from 2 to 6 carbon atoms, or cycloalkyl of from 5 to 7 carbon atoms, or $R^1$ and $R^2$, taken together, represent $-(CH_2)_m-$, in which m is an integer of from 4 to 6; and $R^3$, $R^4$, $R^5$, and $R^6$, which may be the same or different, each represent hydrogen, alkyl of from 1 to 4 carbon atoms, hydrocarbon aryl, or $CCl_3$, or $R^3$ and $R^5$ or $R^4$ and $R^6$, taken together, represent $-(CH_2)_n-$, in which n is an integer of from 3 to 5, and the preparation thereof.

These and other objects of the invention will become more apparent in the discussion below.

DETAILED DESCRIPTION OF THE INVENTION

Applicants' invention is directed to 2-(3-iodo-2-propynyloxy)-ethyl carbamates of the formula

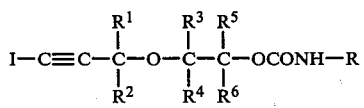

wherein

R is hydrogen, linear or branched alkyl of from 1 to 12 carbon atoms, cycloalkyl of from 4 to 8 carbon atoms, hydrocarbon aryl, halogen or lower alkyl substituted hydrocarbon aryl, hydrocarbon aralkyl, or hydrocarbon arylsulfonyl;

$R^1$ and $R^2$, which may be the same or different, each are hydrogen, linear or branched alkyl of from 1 to 6 carbon atoms, or alkenyl of from 2 to 6 carbon atoms, or cycloalkyl of from 5 to 7 carbon atoms, or $R^1$ and $R^2$, taken together, represent $-(CH_2)_m-$, in which m is an integer of from 4 to 6; and $R^3$, $R^4$, $R^5$, and $R^6$, which may be the same or different, each represent hydrogen, alkyl of from 1 to 4 carbon atoms, or hydrocarbon aryl, or $CCl_3$, or $R^3$ and $R^5$ or $R^4$ and $R^6$, taken together, represent $-(CH_2)_n-$, in which n is an integer of from 3 to 5.

This invention is also directed to the preparation of the compounds of Formula I by reacting alcohols of the formula

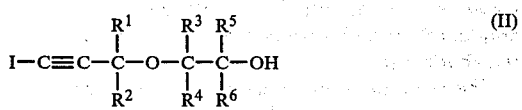

with equimolar amounts of suitable isocyanates of the formula

wherein R and $R^1$ to $R^6$ are as defined above, as well as to the use of the compounds of Formula I as antimicrobial substances.

Examples of linear or branched alkyl of from 1 to 6 carbon atoms or alkenyl of from 2 to 6 carbon atoms, represented by $R^1$ and/or $R^2$, include methyl, ethyl, propyl, isopropyl, n-butyl, isobutyl, sec.butyl, tert.butyl, pentyl, and hexyl groups and branched isomers thereof, as well as vinyl, allyl, propenyl, butenyl, pentenyl, and hexenyl groups and the respective isomers of the alkenyls mentioned having 4, 5, or 6 carbon atoms. Examples of cycloalkyl radicals with from 5 to 7 carbon atoms, represented by $R^1$ and/or $R^2$, include cyclopentyl, cyclohexyl, and cycloheptyl groups. Compounds of Formula I in which both $R^1$ and $R^2$ are either hydrogen or methyl, as well as those compounds in which one of $R^1$ and $R^2$ is hydrogen while the other is methyl, are preferred.

$R^3$, $R^4$, $R^5$, and $R^6$ may each represent, for example, a methyl, ethyl, propyl, isopropyl, n-butyl, isobutyl, sec.-butyl, or tert.butyl group, with a methyl group being preferred. Examples of aryl radicals represented by these substituents include phenyl and naphthyl groups.

Preferred compounds of Formula I are those in which at least four of the radicals $R^1$ to $R^6$ represent hydrogen.

Examples of linear or branched alkyl radicals of from 1 to 12 carbon atoms, represented by R, include methyl, ethyl, propyl, isopropyl, n-butyl, isobutyl, sec.butyl, tert.butyl, pentyl, hexyl, heptyl, octyl, nonyl, decyl, undecyl, and dodecyl groups, as well as the branched isomers of the alkyl radicals having from 5 to 12 carbon atoms. If R is a cycloalkyl of from 4 to 8 carbon atoms, it may, for example, be a cyclobutyl, cyclopentyl, cyclohexyl, cycloheptyl, or cyclooctyl group. Examples of aryl and substituted aryl radicals represented by R include phenyl, naphthyl, tolyl, chlorophenyl, bromophenyl, fluorophenyl, dichlorophenyl, and trichlorophenyl groups, while examples of aralkyl and arylsulfonyl radicals represented by R include benzyl and p-toluene-sulfonyl groups.

Compounds in which R represents a lower alkyl radical of from 1 to 4 carbon atoms, an aryl radical, or an aryl radical with chlorine or bromine substitution, are preferred. Especially preferred compounds are those in which R represents, for example, a propyl, butyl, or phenyl group.

The N-substituted 2-(3-iodo-2-propynyloxy)-ethyl carbamates of Formula I are synthesized according to well-known procedures (Houben-Weyl, *Methoden der*

*Org. Chemie,* Vol. 8 (1952), pp. 141–144) by reacting the alcohols of Formula II with equimolar amounts of suitable, that is, commercially available, isocyanates of Formula III. The reaction is carried out at temperatures from about 10° to 70° C., preferably from about 20° to 30° C., usually in an inert solvent. Examples of suitable solvents include ethylene chloride, dimethyl formamide, toluene, chlorobenzene, methylene chloride, and tetrahydrofuran.

The reactions can be accelerated with catalysts such as, for example, dibutyltin dilaurate. Additional catalysts that may be used include dibutyltin diacetate and tertiary bases such as triethylamine.

The alcohols of Formula II can be prepared, by use of well-known methods, in two reaction steps by the reaction of propargylol or substituted propargylols with ethylene oxide or substituted epoxides, followed by iodoation of the obtained propynyloxy alcohols. Some of the alcohols of Formula II represent novel compounds that are the subject of a commonly assigned, co-pending U.S. patent application Ser. No. 427,888, filed Sept. 29, 1982, incorporated herein by reference.

Examples of the alcohols of Formula II include the following:
a. 2-(3-iodo-2-propynyloxy)-ethanol,
b. 2-(4-iodo-3-butyn-2yloxy)-ethanol,
c. 1-(3-iodo-2-propynyloxy)-2-propanol, and
d. 1-(2-hydroxyethoxy)-1-iodoethynyl cyclohexane.

The isocyanates of Formula III can be, for example, methyl isocyanate, ethyl isocyanate, propyl isocyanate, butyl isocyanate, phenyl isocyanate, 4-chlorophenyl isocyanate, cyclohexyl isocyanate, 4-fluorophenyl isocyanate, 3,4-dichlorophenyl isocyanate, 2,4,5-trichlorophenyl isocyanate, or p-toluene sulfonyl isocyanate.

Due to their microbiostatic and microbiocidal effect, the compounds according to the invention are suitable, for example, for the preservation of technical products, such as paints, glues, dispersions, or cold lubricants, or for the antimicrobial treatment of joint caulking compounds, such as silicon caulks. They are also suitable for the elimination of mold, for example, mold on wet walls, ceilings, or floors, for the preservation of wood, and for the antimicrobial treatment of plastics, such as polyvinyl chloride (PVC) foils. Furthermore, the compounds according to the invention can be used as disinfectants or as preservatives for cosmetics.

For use in antimicrobial agents, one or more compounds according to the invention can be incorporated by a known method into liquid, paste, or solid preparations that are in the form of solutions, suspensions, or emulsions. In preparations ready for use the compounds of the invention should be present in amounts of from about 0.1 to 5 percent by weight based upon the weight of the total antimicrobial preparation. Concentrates for the make-up of such ready-for-use preparations may contain the compounds of the invention in amounts of up to 50 percent by weight, based upon the weight of the total concentrate. The remainder of the antimicrobial preparation will be comprised of conventional formulation ingredients, such as, for example, water, organic solvents such as, for example ethanol, isopropanol, acetone, toluene and ethyl acetate, surfactants and builders.

When the antimicrobial agents are admixed with a desired substance for preservation purposes, the compounds according to the invention should comprise from about 0.001 to 5 percent by weight, preferably from about 0.01 to 3 percent by weight, based upon the weight of the total preparation. In most instances an antimicrobial agent such as is described above will be admixed with the desired substance. However, it is within the scope of the invention that one or more compounds of Formula I could be added directly.

The examples below are intended to illustrate the invention and should not be construed as limiting the invention thereto.

EXAMPLES

EXAMPLE 1

2-(3-Iodo-2-propynyloxy)-ethyl N-methyl-carbamate (Compound A)

One milliliter of dibutyltin dilaurate was added under agitation as catalyst to a solution of 3.3 gm (0.058 mol) of methyl isocyanate and 12.8 gm (0.057 mol) of 2-(3-iodo-2-propynyloxy)-ethanol in 50 ml ethylene chloride. Due to the exothermic reaction, the temperature rose gradually from room temperature to 30° C. After a reaction time of 16 hours, the solvent was removed by distillation under vacuum, and the yellowish oil obtained was extracted with n-hexane to separate the catalyst, the hexane phase being discarded. Then, the residual solvent was removed under vacuum, and 15.6 gm of 2-(3-iodo-2-propynyloxy)-ethyl N-methyl-carbamate (97% of theory) were obtained as a clear, yellowish oil, which crystallized into a colorless solid (melting point: 52°–55° C). Solubility: dissolves readily in ethanol or acetone; almost insoluble in water.

$C_7H_{10}INO_3$ (MW: 283.07) 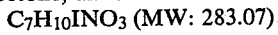

| Analysis (%): | C | H | I |
|---|---|---|---|
| Calculated: | 29.7 | 3.56 | 44.83 |
| Found: | 29.90 | 3.60 | 43.8 |

IR (film; $cm^{-1}$): 2185 ($C\equiv C$), 1710 (s, O—CO—N) no R—NCO—band.

$^1$H—NMR (CDCl$_3$): $\delta=2.8$(d, 3H, J=2.5 Hz, CH$_3$); 3.6–4.4 (m, 4H, OCH$_2$CH$_2$O); 4.39 (s, 2H, CH$_2$); 4.7–5.2 (wide, NH).

EXAMPLE 2

2-(3-Iodo-2-propynyloxy)-ethyl N-(4-chlorophenyl)-carbamate (Compound G)

The procedure described in Example 1 was followed. The reaction batch was comprised as follows:
4.6 gm (0.03 mol) of 4-chlorophenyl isocyanate;
6.8 gm (0.03 mol) of 2-(3-iodo-2-propynyloxy)-ethanol;
50 ml of ethylene chloride; and
1 ml of dibutyltin dilaurate.
The yield was 10.8 gm (95% of theory) of a yellow solid with a melting point of 56°–60° C.

$C_{12}H_{11}ClINO_3$ (MW: 397.58) 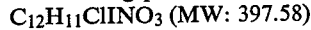

| Analysis (%): | C | H | N | I |
|---|---|---|---|---|
| Calculated: | 37.97 | 2.92 | 3.69 | 33.43 |
| Found: | 38.3 | 3.01 | 3.49 | 32.2 |

IR(KBr; $cm^{-1}$): 2180 ($C\equiv C$), 1712 (s, OCON); no R—NCO—band.

$^1$H—NMR (D$_6$—DMSO): $\delta=3.4$—4.3 (m, 4H, OCH$_2$CH$_2$O); 4.3 (s, 2H, CH$_2$); 7.16–7.58 (m, 4H, aromat. H).

EXAMPLE 3

2-(3-Iodo-2-propynyloxy)-ethyl N-ethyl-carbamate (Compound B)

The procedure described in Example 1 was followed. The reaction batch was comprised as follows:
3.0 gm (0.042 mol) of ethyl isocyanate,
9.5 gm (0.042 mol) of 2-(3-iodo-2-propynyloxy)-ethanol,
50 ml of ethylene chloride, and
1 ml of dibutyltin dilaurate.
A light yellow oil was obtained, in an amount of 11.9 gm (95% of theory).
$n_D^{20} = 1.5282$
$C_8H_{12}INO_3$ (MW: 297.09)

| Analysis (%): | C | H | I |
|---|---|---|---|
| Calculated: | 32.34 | 4.07 | 42.71 |
| Found: | 33.0 | 4.17 | 41.1 |

IR (film; cm$^{-1}$): 2182 (C≡C), 1702(s,OCON); no R—NCO—band.

$^1$H—NMR (CDCl$_3$): δ=1.18 (t, 3H, J=3.5 Hz, CH$_3$), 3.0–3.5 (m, 2H, J=3.5 Hz, and 1 Hz, CH$_2$N); 3.64–4.35 (m, 4H, OCH$_2$CH$_2$O); 4.35 (s, 2H, CH$_2$O); 4.6—5.2 (wide, NH).

By following the procedure described in Example 1, additional compounds were prepared, which compounds are reflected in Tables I and II below. For the sake of convenience, the compounds prepared according to Examples 1 to 3 have been included in Table I as Compounds A, G, and B, respectively.

TABLE I

I—C≡C—CH$_2$—O—CH$_2$—CH$_2$—OCONH—R  (Ia)

| Compound | R | Melting Point (°C.) or n$_D^{20}$ | Yield (%) |
|---|---|---|---|
| A | CH$_3$ | 52–55 | 97 |
| B | —CH$_2$CH$_3$ | 1.5282 | 95 |
| C | —(CH$_2$)$_3$CH$_3$ | 1.5183 | 98 |
| D | —C(CH$_3$)$_3$ | 1.5132 | 89 |
| E | cyclohexyl | 86–88 | 75 |
| F | phenyl | 101–104 | 82 |
| G | —C$_6$H$_4$—Cl | 56–60 | 95 |
| H | —SO$_2$—C$_6$H$_4$—CH$_3$ | light yellow, highly viscous resin | 92 |
| I | —C$_6$H$_3$(Cl)(Cl) | 75–77 | 95 |
| J | —C$_6$H$_4$—F | 67–69 | 94 |
| K | —C$_6$H$_2$(Cl)(Cl)(Cl) | 112–115 | 55 |
| L | H | 74–76 | 82 |

TABLE II

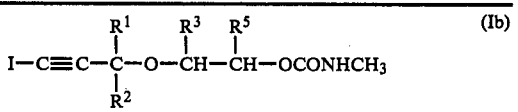

| Compound | R$^1$ | R$^2$ | R$^3$ | R$^5$ | Melting Point (°C.) or n$_D^{20}$ | Yield (%) |
|---|---|---|---|---|---|---|
| M | H | H | CH$_3$ | CH$_3$ | 1.5202 | 100 |
| N | CH$_3$ | H | H | H | 1.5112 (at 50° C.) | 100 |
| O | CH$_3$ | CH$_3$ | H | H | 79 | 82 |
| P | CH$_3$ | H | CH$_3$ | CH$_3$ | 1.4910 (at 50° C.) | 83 |

Antimicrobial Effectiveness of the Compounds of General Formula I

The microbistatic effectiveness of the compounds A to P was determined with suspensions of the following test organisms:

| Organism | Concentration (organisms/ml) |
|---|---|
| 1. Staphylococcus aureus | 2 × 10$^9$ |
| 2. Escherichia coli | 2 × 10$^9$ |
| 3. Pseudomonas aeruginosa | 5 × 10$^8$ |
| 4. Candida albicans | 2 × 10$^8$ |
| 5. Aspergillus niger | 5 × 10$^7$ |
| 6. Penicillium camerunense | 5 × 10$^7$ |
| 7. Trichophyton mentagrophytes | 2 × 10$^7$ |
| 8. Penicillium funiculosum | 5 × 10$^7$ |

The inhibitory concentrations of the compounds to be tested were established by use of the dilution test according to the guidelines for the testing of chemical disinfectants by the Deutsche Gesellschaft für Hygiene and Mikrobiologie (German Society for Hygiene and Microbiology), 1972. Sterile test tubes containing Standard-I-Bouillon (pH 7.5, available from Merck) (standard-I-broth) or Würze-Bouillon (pH 5.5, available from Merck, 8° BG) (malt broth) were used for the tests. After addition of the active substances, the nutrient solution volumes in the test tubes were 10 ml, respectively. Then, 0.1 ml of each test organism suspension in the specified concentration was transferred to the test tubes. The nutrient solution samples inoculated with bacteria were kept in an incubator for three days at 37° C. The samples inoculated with molds were incubated 3 to 4 days at 30° C. Then, the concentration of active substance added to the nutrient medium that still barely inhibited the growth of the organisms was determined. The value established by this method was the inhibitory concentration. Active substance concentrations of 1,000, 500, 250, 100, 50, and 10 ppm were tested; in addition, for some of the molds concentrations of 25, 10, 5, 2.5, and 1 ppm were also tested.

The inhibitory concentrations determined for Compounds A to P by liquid inhibitory series for the determination of the microbiostatic action, are set forth in the following table:

TABLE III

| Compound | Test Organism (ppm) | | | | | | | |
|---|---|---|---|---|---|---|---|---|
| | 1 | 2 | 3 | 4 | 5 | 6 | 7 | 8 |
| A | 500 | 500 | 500 | 25 | 5 | 50 | 5 | 10 |
| B | 500 | 1000 | 1000 | 25 | 2.5 | 50 | 2.5 | 10 |
| C | 250 | X* | 1000 | 25 | 2.5 | 50 | 2.5 | 10 |
| D | 1000 | X | X | 50 | ≦10 | 50 | 10 | 50 |
| E | X | X | X | 25 | 10 | 50 | 5 | 50 |
| F | X | X | X | 25 | 2.5 | 10 | 1 | 10 |
| G | 50 | 500 | X | ≦10 | 2.5 | 5 | 10 | 10 |
| H | 500 | X | 1000 | 250 | 50 | 100 | — | — |
| I | ≦10 | X | X | 50 | ≦10 | ≦10 | — | — |
| J | 50 | X | X | 50 | ≦10 | ≦10 | — | — |
| K | X | X | X | 500 | 100 | 100 | — | — |
| L | 500 | 250 | 1000 | 50 | ≦10 | 50 | — | — |
| M | 100 | 1000 | X | 100 | ≦10 | 50 | — | — |
| N | 500 | 500 | X | 100 | ≦10 | 50 | — | — |
| O | 500 | 1000 | X | 250 | 100 | 50 | — | — |
| P | X | 500 | X | 250 | 250 | 50 | — | — |

*X = >1000 ppm

The microbiocidal action of Compounds A to P was determined against the following suspensions of test organisms:

| Organism | Concentration (organisms/ml) |
|---|---|
| 1. Aspergillus niger | 5 × 10$^7$ |
| 2. Penicillium camerunense | 5 × 10$^7$ |

The times required by the test products to develop the microbiocidal action were determined by the suspension test according to the guidelines for the testing of chemical disinfectants of the Deutsche Gesellschaft für Hygiene und Mikrobiologie, 1972. The substances to be tested were first dissolved in a small amount of alcohol. The ethanolic solutions were diluted with hard water of 17° dH hardness to produce test solutions with contents of 3000 ppm and 500 ppm active substance, respectively, and a maximum of 1 percent by weight of ethanol. At room temperature, 0.1 ml of the test organism suspension was pipetted into test tubes. Ten milliliters of the test solution described above were added to each tube. After standing for 15, 60, and 120 minutes at room temperature, one drop of material was removed from each test tube with a loop, and 10 ml of nutrient solution containing 3 percent by weight of Tween ®80 (surface active substance available from Atlas Chemical Industries, Inc.) and 0.3 percent by weight of lecithin as deinhibitor were inoculated with it. Standard-I-Bouillon in a 1 percent by weight concentration was used as nutrient medium. The samples were incubated at 30° C. After not less than five days, the growth on the cultures was examined macroscopically, and the microbiocidal times compiled in Table IV below were determined by this method.

TABLE IV

| Compound | Concentration (ppm) | Microbiocidal Action (min.) | | pH |
|---|---|---|---|---|
| | | Organism 1 | Organism 2 | |
| A | 3000 | ≦15 | ≦15 | 4.3 |
| | 500 | 120 | ≦15 | — |
| B | 3000 | ≦15 | ≦15 | 4.1 |
| | 500 | 120 | 60 | — |
| C | 3000 | ≦15 | 60 | 3.9 |
| | 500 | 120 | X* | — |
| D | 3000 | ≦15 | ≦15 | 4.0 |
| | 500 | 120 | ≦15 | — |
| E | 3000 | X | X | 5.3 |
| | 500 | X | X | — |
| F | 3000 | 120 | X | 5.5 |
| | 500 | X | X | — |
| G | 3000 | ≦15 | ≦15 | 7.1 |
| | 500 | X | X | — |
| H | 3000 | X | ≦15 | 3.3 |
| I | 3000 | X | X | 5.3 |
| J | 3000 | 60 | X | 7.1 |
| | 500 | 120 | X | — |
| K | 3000 | 60 | 60 | 7.7 |
| | 500 | X | X | 7.4 |
| L | 3000 | ≦15 | ≦15 | 5.7 |
| | 500 | 60 | ≦15 | 6.2 |
| M | 3000 | X | ≦15 | 4.2 |
| | 500 | — | X | 4.8 |
| N | 3000 | ≦15 | ≦15 | 4.5 |
| | 500 | X | X | 5.1 |
| O | 3000 | ≦15 | ≦15 | 4.5 |
| | 500 | 120 | 60 | 5.1 |
| P | 3000 | X | 120 | 4.6 |
| | 500 | X | X | 5.0 |

*X = >120 minutes

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A compound of the formula

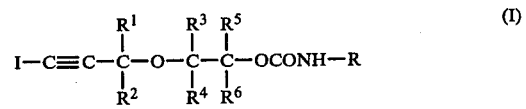

(I)

wherein
R is hydrogen, linear or branched alkyl of from 1 to 12 carbon atoms, cycloalkyl of from 4 to 8 carbon atoms, phenyl or naphthyl, either unsubstituted or halogen or lower alkyl substituted, benzyl, or p-toluene-sulfonyl;

$R_1$ are $R_2$, which may be the same or different, each are hydrogen, linear or branched alkyl of from 1 to 6 carbon atoms or alkenyl of from 2 to 6 carbon atoms, or cycloalkyl of from 5 to 7 carbon atoms, or $R^1$ and $R^2$, taken together, represent —(CH$_2$)$_m$—, in which m is an integer of from 4 to 6; and $R^3$, $R^4$, $R^5$, and $R^6$, which may be the same or different, each represent hydrogen, alkyl of from 1 to 4 carbon atoms, phenyl, naphthyl or CCl$_3$, or $R^3$ and $R^5$ or $R^4$ and $R^6$, taken together, represent —(CH$_2$)$_n$—, in which n is an integer of from 3 to 5.

2. A compound of claim 1, wherein $R^1$ and $R^2$ are both methyl or hydrogen or one of $R^1$ and $R^2$ is hydrogen and the other is methyl.

3. A compound of claim 1, wherein at least 4 of $R^1$ to $R^6$ represent hydrogen.

4. A compound of claim 1, wherein R is alkyl of 1 to 4 carbon atoms, phenyl, naphthyl, or halogen substituted phenyl or naphthyl.

5. A compound of claim 1, wherein when R is halogen or lower alkyl substituted phenyl, R is tolyl, chlorophenyl, bromophenyl, fluorophenyl, dichlorophenyl, or trichlorophenyl.

6. The compound of claim 1 which is 2-(3-iodo-2-propynyloxy)-ethyl N-methyl-carbamate.

7. The compound of claim 1 which is 2-(3-iodo-2-propynyloxy)-ethyl N-(4-chlorophenyl)-carbamate.

8. The compound of claim 1 which is 2-(3-iodo-2-propynyloxy)-ethyl N-ethyl-carbamate.

9. An antimicrobial composition for limiting the growth of microbial organisms which consists essentially of an antimicrobial effective amount of one or more compounds of claim 1 and conventional formulating substances.

10. A process for inhibiting the growth of microbial organisms which comprises contacting said organisms with an antimicrobial effective amount of one or more compounds of claim 1.

* * * * *

UNITED STATES PATENT AND TRADEMARK OFFICE
CERTIFICATE OF CORRECTION

PATENT NO. : 4,474,807

DATED : October 2, 1984

INVENTOR(S) : WERNER GERHARDT et al.

It is certified that error appears in the above-identified patent and that said Letters Patent is hereby corrected as shown below:

Title page, [73] should read:

-- Assignee: Henkel Kommanditgesellschaft auf Aktien, Düsseldorf-Holthausen, Fed. Rep. of Germany --

Signed and Sealed this

Eighth Day of October 1985

[SEAL]

Attest:

Attesting Officer

DONALD J. QUIGG

Commissioner of Patents and Trademarks—Designate